(12) United States Patent
McMullen et al.

(10) Patent No.: US 6,283,944 B1
(45) Date of Patent: *Sep. 4, 2001

(54) INFUSION SYSTEMS WITH PATIENT-CONTROLLED DOSAGE FEATURES

(75) Inventors: Ray McMullen, Shorewood; Paul Kratoska, N. Brooklyn Park; Anthony Gardner, Minneapolis, all of MN (US)

(73) Assignee: Medtronic, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/070,051

(22) Filed: Apr. 30, 1998

(51) Int. Cl.[7] ........................................... A61M 1/00
(52) U.S. Cl. ..................... 604/151; 604/142; 604/183; 604/891.1
(58) Field of Search .................. 604/93.01, 131, 604/132, 141, 142, 151, 153, 891.1

(56) References Cited

U.S. PATENT DOCUMENTS

| | | |
|---|---|---|
| 4,714,462 * | 12/1987 | DiDomenico . |
| 5,085,644 * | 2/1992 | Watson et al. .......................... 604/93 |
| 5,152,753 * | 10/1992 | Laguette et al. ................... 604/891.1 |
| 5,445,616 | 8/1995 | Kratoska et al. . |
| 5,505,707 | 4/1996 | Manzie et al. . |
| 5,575,770 | 11/1996 | Melsky et al. . |
| 5,607,418 * | 3/1997 | Arzbaecher ........................ 604/891.1 |

FOREIGN PATENT DOCUMENTS

| | | |
|---|---|---|
| 9012609 | 1/1990 | (WO) . |
| 9723252 | 3/1997 | (WO) . |

OTHER PUBLICATIONS

PCT International Search Report.
A1 Medtronic Brochure © 1996, AlgoMed Infusion System Model 84112, Pain Relief at Their Fingertips.

* cited by examiner

Primary Examiner—Anhtuan T. Nguyen
Assistant Examiner—Michael M. Thompson
(74) Attorney, Agent, or Firm—Banner & Witcoff, Ltd.

(57) ABSTRACT

An infusion system delivers drug to the patient at a fixed rate while permitting the patient to introduce a controlled bolus dosage when needed. A pump having a bulkhead that is provided with first and second flow paths from the pump reservoir to a single outlet port. The first flow path communicates with a first flow regulator which restricts flow in the first flow path to the desired fixed rate of delivery. The second flow path communicates with a patient-operated pump incorporated into the pump housing. The patient-operated pump may be in the form of a deformable reservoir that accumulates a drug bolus which may be expelled when the reservoir is compressed by the patient's fingers. A second flow regulator may be incorporated in the drug flow path upstream of the patient-operated pumping device to restrict the dosage that may accumulate therein. Additionally, a fluid control assembly incorporating a patient-controlled pump may be used with single or dual port pumps.

20 Claims, 4 Drawing Sheets

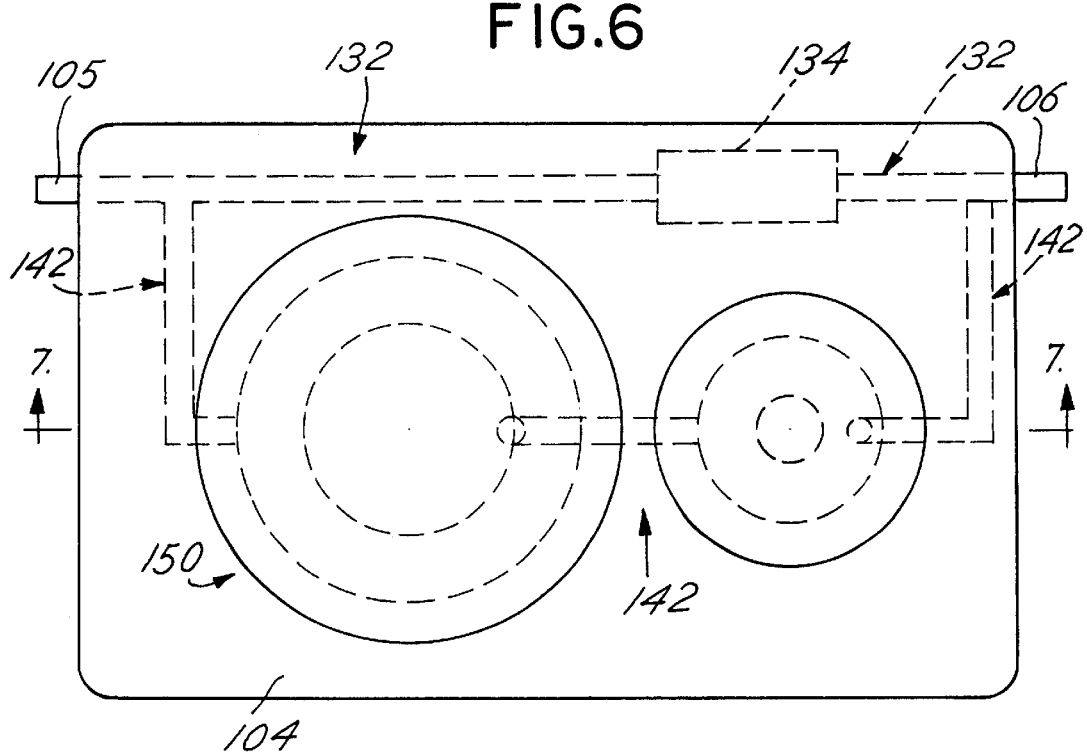
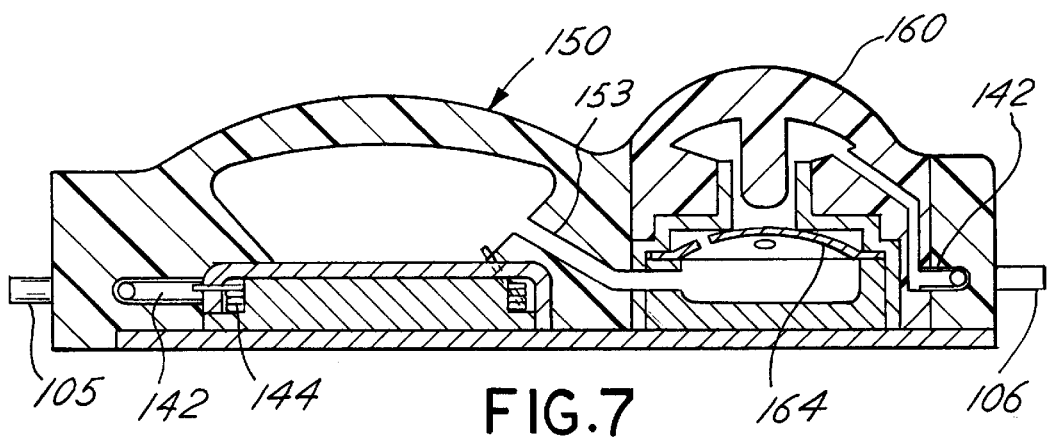

INFUSION SYSTEMS WITH PATIENT-CONTROLLED DOSAGE FEATURES

FIELD OF THE INVENTION

The present invention relates to drug delivery devices for delivering drugs to the body of a patient. More particularly, the present invention relates an implantable drug infusion system that delivers a fixed flow of drug and permits patient control of additional drug dosage.

BACKGROUND OF THE INVENTION

The use of implantable drug infusion systems is well-known. These systems provide steady, long-term delivery of drug therapy to the human body. They also eliminate the need for frequent intravenous drug injections. Each system typically includes a refillable drug reservoir and flow control device for regulating the drug delivery rate.

One form of drug infusion system incorporates an implantable pump such as that disclosed in U.S. Pat. Nos. 5,445,616 and 5,575,770. The subject matter of both patents is incorporated herein by reference. Pump-based systems provide constant flow of drug to the patient at very low rates. These pumps may be fixed rate pumps or programmable pumps. In the case of fixed-rate, adjustment of the delivery rate and therefore the drug dosage may not be altered. In case of programmable pumps, reprogramming of the pump controller by a physician is required for changes in pump rate.

There is a current trend towards providing some degree of patient control in implantable drug infusion systems. Clinical studies show that actual drug usage may be reduced if a patient believes that he or she has some degree of control over drug dosage. A terminally-ill patient who has no ability to control or self-administer a drug will frequently insist on additional dosage at each visit to a physician as a precaution against exhaustion of the drug supply before the patient's next office visit. In addition to these patient psychological aspects, there are added benefits of patient control. For example, in progressive diseases, the development of breakthrough pain may require immediate increase in drug dosage. Similarly, a diabetic patient may need to tailor insulin dosage to maintain blood glucose levels through a changing diet. The ability to self-administer drug therapy may therefore reduce the number of office visits and provide immediate drug dosage increase when needed.

There have been prior efforts to provide drug infusion systems that offer patient controlled dosage features. One known form of drug infusion system which includes patient controlled dosage features is a drug infusion pad, such as that disclosed in U.S. Pat. No. 5,085,644, which permits a patient to self-administer drug therapy. Typically, this patient control of dosage is in the form of a deformable chamber which may be compressed by the patient to deliver an intermittent supply of drug to the body. The infusion pad is implanted subcutaneously, usually over the rib cage to provide support against the forces of a patient's fingers compressing the reservoir. Known drug infusion pads, however, only provide for intermittent delivery of drug therapy and are therefore undesirable in applications where a steady flow of drug is desired. The patient must continuously activate the infusion pad to receive medication. For example, U.S. Pat. No. 5,085,644 discloses a patient-controlled infusion device which utilizes a deformable pumping chamber to permit a patient to intermittently administer a supply of drug from a main reservoir. The disclosed device utilizes a fluid flow restrictor to limit the recharge rate of the pumping chamber.

There is a yet unaddressed need in the medical field for a drug infusion system which offers the benefits of both fixed-rate delivery systems and patient control of dosage. Such a system would find application in therapy delivery for example, for cancer patients, who may need a fixed rate of drug delivered constantly and the ability to administer themselves a bolus of drug when "breakthrough" pain occurs. Similarly, a diabetic patient may need, in addition to a steady supply of insulin, an additional dosage when the patient's diet has resulted in a lower than anticipated blood glucose level.

It would therefore be desirable to provide a drug infusion system which provides patient-control features in addition to the advantages offered by fixed rate delivery systems.

SUMMARY OF THE INVENTION

The invention provides an infusion system that delivers drug to the patient at a fixed rate and permits the patient to introduce a controlled bolus dosage when needed. In one preferred embodiment, the invention resides in a pump having a bulkhead that is provided with first and second flow paths from the pump reservoir to a single outlet port. The first flow path communicates with a first flow regulator which restricts flow in the first flow path to the desired fixed rate of delivery. The second flow path communicates with a patient-operated pumping device incorporated into the pump housing. The patient-operated pumping device may be in the form of a deformable reservoir that accumulates a drug bolus which may be expelled when the reservoir is compressed by the patient's fingers. A second flow regulator may be incorporated in the drug flow path upstream of the patient-operated pumping device to restrict the dosage that may accumulate therein. A safety valve may also be incorporated into the pump housing in downstream fluid communication with the patient-operated pumping device to prevent accidental discharge of the drug bolus.

In another preferred embodiment, the invention resides in a fluid control assembly that may be used with single or dual port pumps. The fluid control assembly comprises a body with an inlet port and an outlet port. Two fluid control paths are defined within the body between the ports. A first fluid control path is provided with a first flow regulator for regulating a fixed flow rate of drug between the inlet and outlet ports. A second fluid control path is in fluid communication with a patient-controlled pumping device which accommodates a bolus of drug that may be expelled by the patient. Both first and second fluid control paths communicate with the inlet port and outlet port. A second flow regulator is disposed in the second flow path to limit the rate of accumulation of the drug bolus. The reservoir communicates with the flow controller outlet port via a safety valve which prevents accidental discharge of the drug bolus.

Advantageously, the invention provides an infusion system that offers both a fixed rate of delivery and the capability for a patient to deliver a drug bolus when needed within safe dosage levels. Other objects, advantages novel features, and the further scope of applicability of the present invention will be set forth in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings, in which like numbers refer to like parts throughout:

FIG. 6 is a top view of a fluid control assembly according to the embodiment shown in FIG. 5.

FIG. 7 is a cross-section taken along lines 7—7 of FIG. 6.

DETAILED DESCRIPTION OF THE PREFERRED EMBODIMENTS

Figure 1:
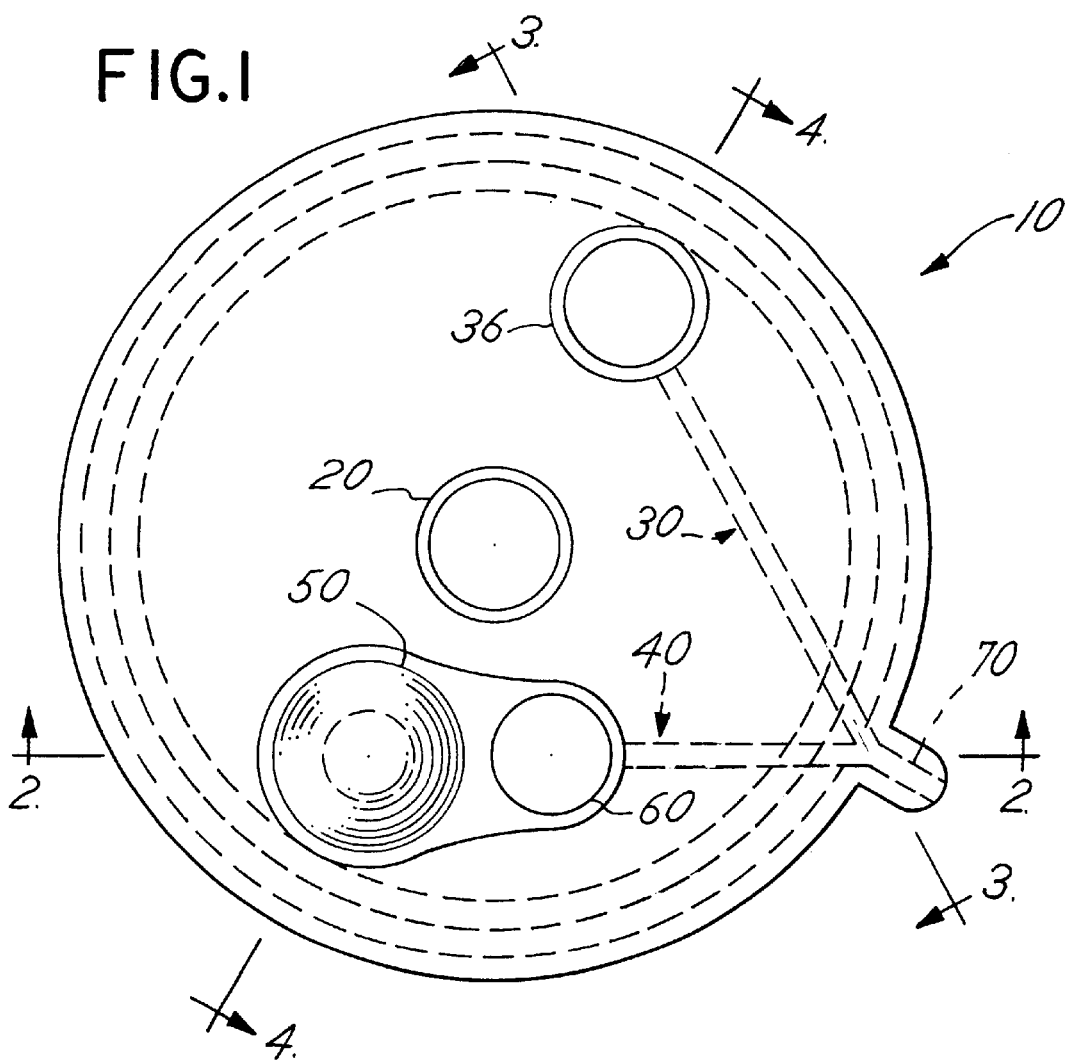
FIG. 1 is a top view of a pump according to a preferred embodiment of the present invention.
Figure 2:
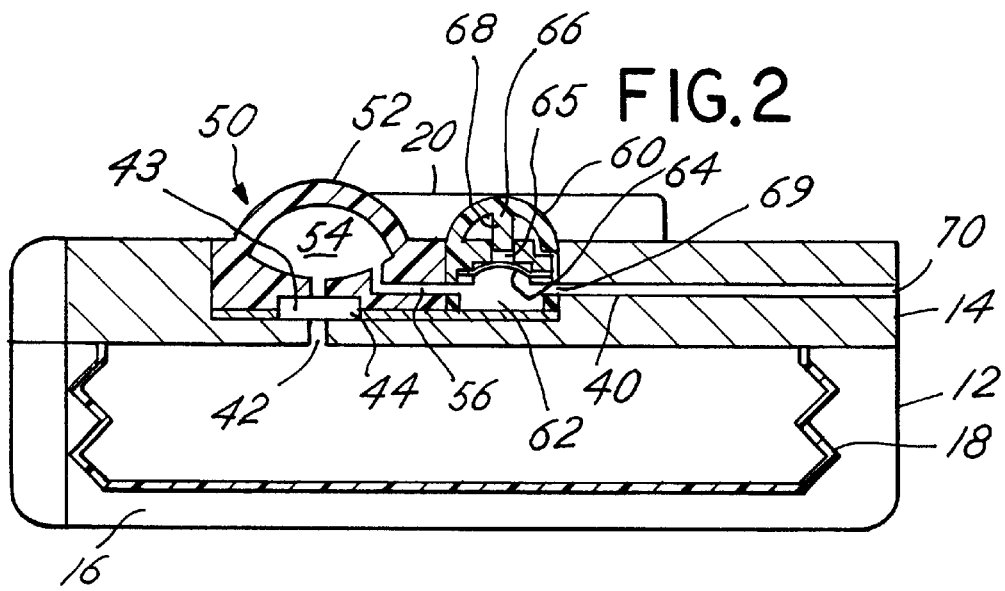
FIG. 2 is a cross-section taken along lines 2—2 of FIG. 1.

Referring to FIGS. 1–4, an implantable pump 10 according to a preferred embodiment of the present invention comprises a pump housing 12 which, in conjunction with bulkhead 14, defines a bellows chamber 16 housing a bellows reservoir 18. Associated with bulkhead 14 are a number of features, including refill port 20, first flow path 30, second flow path 40, patient-controlled pump 50 and safety valve 60. Each of these features and their functional relationships will be described in detail below.

Bellows 18 forms with the lower surface of bulkhead 14 a variable volume reservoir for containing a supply of drug. The drug supply may be introduced through refill port 20 which includes a septum 22. A catheter or needle may be inserted through septum 22 to convey drug from an external supply (not shown) to refill chamber 24, through refill conduit 26 and into the interior of bellows 18.

First flow path 30 and second flow path 40 are in fluid communication with bellows 18 through first reservoir outlet 32 and second reservoir outlet 42, respectively. Both flow paths 30 and 40 provide separate fluid communication from the interior of bellows to pump outlet port 70. As will be further explained below, first flow path provides a fixed delivery rate from bellows 18 to pump outlet port 70, while second flow path 40 provides a patient-controlled dosage to pump outlet port 70.

The term "path" as used herein refers to the element or elements which provide a conduit or passage through which fluid may be conveyed. The term "in fluid communication" as used herein refers to a structural relationship between elements which permits conveyance of fluid therebetween and does not necessarily imply the presence of a fluid. The term "fluid" as used herein refers to a liquid or gaseous material or a material which includes components which are liquid or gaseous or both.

Figure 3:
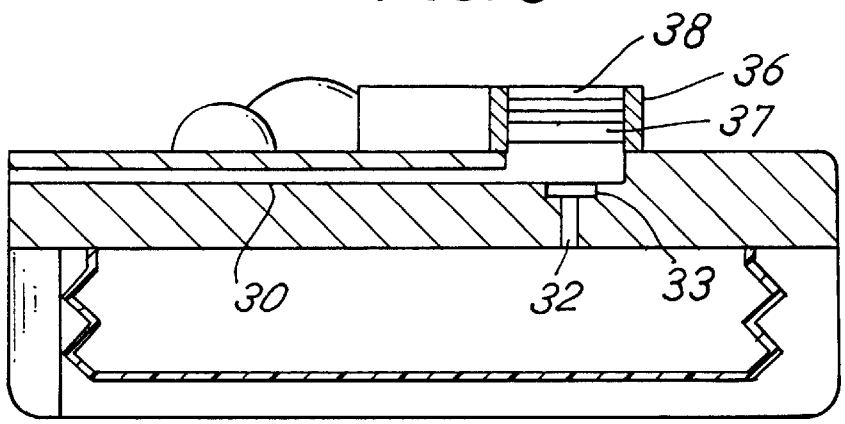
FIG. 3 is a cross-section taken along lines 3—3 of FIG. 1.

Referring particularly to FIG. 3, first flow path 30 provides a fixed flow rate of drug from reservoir 18 to pump outlet port 70. A first flow regulator 33 is provided in fluid communication with first reservoir outlet port 32 to restrict drug flow to a desired rate. Auxiliary injection port 36 is provided for permitting a physician to introduce drug directly into the first flow path 30. Auxiliary injection port 36 includes an auxiliary septum 37 and a screen 38 for restricting septum access to needles below a predetermined diameter. This is provided as a safety feature to prevent accidental injection of a pump refill supply of drug into auxiliary injection port 36.

Figure 4:
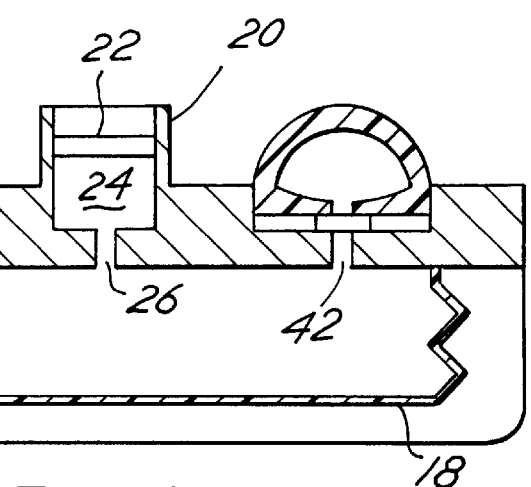
FIG. 4 is a cross-section taken along lines 4—4 of FIG. 1.
Figure 5:
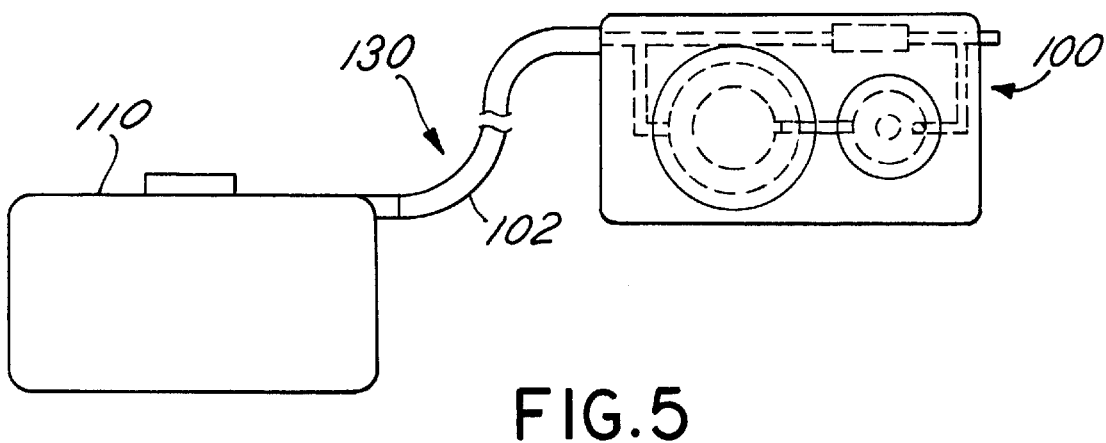
FIG. 5 is a schematic of a drug infusion system according to another preferred embodiment of the present invention.

Referring particularly to FIGS. 1 and 4, second flow path 40 begins at second reservoir outlet 42 which conveys drug via recharge conduit 43 from the bellows 18 to patient-controlled pump 50. Patient-controlled pump is provided in the form of a resilient crown 52 which may be constructed of silicone rubber or a like material which has similar characteristics with regard to flexibility and biocompatibility. Crown 52 defines an inner chamber 54 which is in fluid communication with safety valve 60 via discharge conduit 56.

Drug flow from bellows 18 into chamber 54 is limited by recharge flow regulator 44 disposed in second flow path 40 upstream of chamber 54. Recharge flow regulator 44 may be comprised of a porous flow restrictor or micromachined restrictor. Alternatively, the dimensions of recharge conduit 43 may configured to provide flow-limiting features, for example, by providing a recharge conduit 43 in the form of a capillary passage, or providing a separate capillary tube of suitable length to achieve a desired flow restricting function Safety valve 60 includes a valve inlet chamber 62 defined by a diaphragm 64 which is normally biased upwardly to occlude valve passage 65. Actuator 66 includes a projection 68 for engaging diaphragm 64 and displacing it downward to permit egress of fluid from valve inlet chamber 62 to valve outlet 69 and ultimately to pump outlet port 70. Those of ordinary skill will appreciate that the discharge of the drug bolus from patient-controlled pump 50 requires not only patient-initiated compression of resilient chamber 52, but also simultaneous actuation of safety valve actuator 66. Thus, safety valve 60 functions to prevent unintended discharge of drug from patient-controlled pump 50.

In accordance with the invention, the recharge flow rate into the patient-controlled pump 50 is selected to be a desired percentage of the daily fixed flow rate of drug to the patient. This feature of the invention provides a limit on the patient-administered dosage. For example, recharge flow regulator can be selected to provide 50% of the fixed daily dose of drug. In that case, the patient would be permitted a total dosage per day of 150% of the dosage provided by the fixed flow of drug through second flow path 40.

The present invention also resides in a flow control assembly 100 illustrated in FIGS. 5–8. Flow control assembly 100 may be used to provide the inventive features on single-port pump configurations. Flow control assembly 100 is also useful for providing an infusion system in which it is advantageous to locate the patient control features in an area of the body remote from the location of the pump.

In accordance with the invention, reservoir pump 110 is in fluid communication with flow control assembly 100 via single-lumen catheter 102. Flow control assembly 100 includes a body 104 having an inlet port 105 and an outlet port 106. First fluid control path 132 and second fluid control path 142 are defined within body 104 and provide fixed and patient-controlled flows of drug, respectively, between inlet port 105 and outlet port 106. First fluid control path 132 is provided with a first flow regulator 134 to limit the flow of drug therein to a desired fixed rate. A first flow path 130 is defined by the reservoir pump 110, catheter 102 and first fluid control path 132.

Second fluid control path 142 communicates with a patient-controlled pump 150 having structure identical to that of patient-controlled pump 50, described above with respect to FIGS. 1–4. Recharge flow regulator 144 is provided in the form of a capillary tube coiled beneath pump 150 upstream thereof to limit the flow of drug into patient-controlled pump 150 to a desired value. Second fluid control path 142 is defined within body 104 of flow control assembly 100 and is in fluid communication with first fluid control path 132. In this manner, the patient-controlled dosage can be combined with the fixed rate of flow in first flow path 130. Second flow path 140 is defined by second fluid control path 142.

A safety valve 160 is provided in fluid communication with discharge conduit 153 of flow control assembly 100. The details of safety valve 160 are identical to those described above with respect to safety valve 60 and FIG. 1–3. Through selective deformation of diaphragm 164, safety valve 160 operates to prevent unintended discharge of drug from patient-controlled pump 150.

Figure 8:
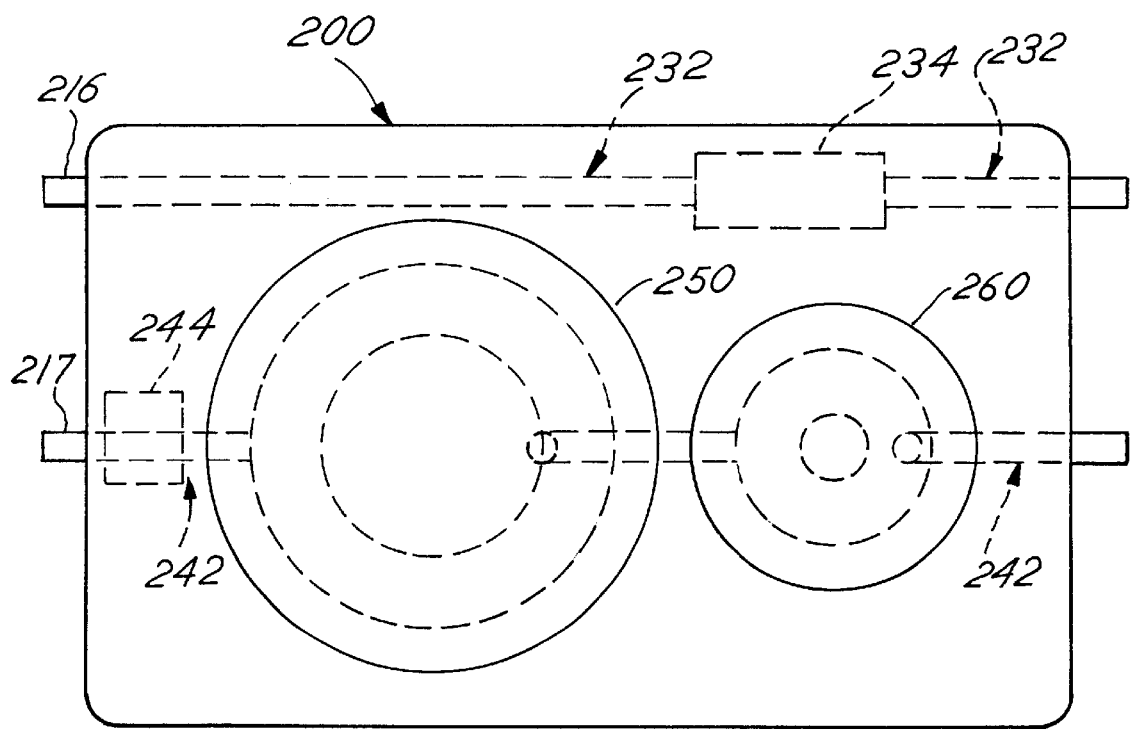
FIG. 8 is a top view of a fluid control assembly according to another preferred embodiment of the invention.

FIG. 8 illustrates another preferred embodiment of the present invention. Flow control assembly 200 is provided for use with a dual port pump (not shown). A double lumen catheter is used to provide fluid communication from the pump ports to respective inlet ports 216 and 217 of flow control assembly 200. First inlet port 216 communicates with a first fluid control path 232 which has a first flow regulator 234 therein to limit flow to a predetermined fixed rate. A second fluid control path 242 is provided with a second flow regulator 244 to limit the recharge rate of flow control assembly 250. Safety valve 260 is provided in second fluid control path 242 to prevent unintentional discharge of drug. It will be appreciated that first fluid control path 232 defines a first flow path in conjunction with a first flow conduit (not shown) in the pump, a first inlet catheter, and a first discharge catheter (not shown). Similarly, second fluid control path 242 defines a second flow path in conjunction with a second flow conduit (not shown) in the pump, a second inlet catheter, and second discharge catheter (not shown). A junction (not shown) will provide fluid communication between the two discharge catheters to combine the respective drug flows and deliver to a single delivery site in the body.

Those skilled in the art will recognize that the preferred embodiments may be altered or amended without departing from the true spirit and scope of the invention, as defined in the accompanying claims.

What is claimed is:

1. A drug delivery system for providing patient control of drug delivery to the patient's body comprising:
    a main pump having a reservoir for containing a supply of drug, wherein the main pump is elected from the group consisting of a fixed-rate pump and a programmable pump;
    a first flow path for delivering a fixed flow of drug from the reservoir to the body by operation of the main pump;
    a second flow path in fluid communication with the reservoir and the first flow path, the second flow path including a patient-controlled pump therein for permitting a patient to supplement the fixed flow of drug with additional drug dosage, wherein the additional drug dosage is provided from the reservoir of the main pump.

2. The drug delivery system according to claim 1, wherein the first and second flow paths are defined in a bulkhead of the pump.

3. The drug delivery system according to claim 2, wherein the patient-controlled pump comprises a resilient pumping chamber in the second flow path.

4. The drug delivery system according to claim 3, further comprising a safety valve for preventing unintended discharge from the patient-controlled pump.

5. The drug delivery system according to claim 3, wherein the patient-controlled pump comprises a resilient pumping chamber in the second flow path.

6. The drug delivery system of according to claim 2, wherein the first flow path is comprised of a first reservoir discharge port in fluid communication with the reservoir port and wherein the second flow path is comprised of a second reservoir discharge port in fluid communication with the reservoir port.

7. The drug delivery system according to claim 2, wherein the main pump comprises a housing and wherein the patient-controlled pump is incorporated into the housing.

8. The drug delivery system according to claim 2, further comprising a safety valve for preventing unintended discharge from the patient-controlled pump.

9. The drug delivery system according to claim 1, further comprising:
    a bulkhead on the pump having an outlet port;
    a catheter in fluid communication with the outlet port;
    a fluid control assembly in fluid communication with the catheter and including a first fluid control path and a second fluid control path defined therein;
    wherein the first flow path is defined by the pump bulkhead, the catheter and the first fluid control path and wherein the second flow path is provided by the second fluid control path.

10. A fluid assembly for use within an implantable pump for permitting patient-control of drug delivery comprising:
    a body defining a first fluid control path and a second fluid control path, wherein the first control path delivers drug from the implantable pump, wherein the implantable pump is selected from the group consisting of a fixed-rate pump and a programmable pump;
    a first flow regulator in the first fluid control path for limiting flow therein to a substantially constant rate;
    a patient-controlled pump in the second fluid control path for permitting a patient to discharge a bolus of drug into the second fluid control path;
    a second flow regulator in the second fluid control path for limiting the recharge rate of the patient-controlled pump.

11. The fluid control assembly according to claim 10, further comprising a safety valve in the second fluid control path for preventing accidental discharge of drug from the patient-controlled pump.

12. The fluid control assembly according to claim 10, further comprising a junction providing fluid communication between the first fluid control path and the second fluid control path.

13. The fluid control assembly according to claim 10, wherein the patient-controlled pump is comprised of a flexible crown.

14. The fluid control assembly according to claim 10, wherein at least one of the first and second flow regulators is comprised of a capillary tube.

15. The fluid control assembly according to claim 10, wherein at least one of the first and second flow regulators is comprised of a micromachined restrictor.

16. A pump for providing patient control of drug delivery to the patient's body comprising:
    a reservoir for containing a supply of drug;
    a first flow path for delivering a substantially fixed flow of drug from the reservoir to the body by operation of the pump, wherein the pump is selected from the group consisting of a fixed-rate pump and a programmable pump; and a patient-controlled pump in fluid communication with the reservoir and the first flow path for delivering a patient-controlled dosage to supplement the drug flow in the first flow path wherein the patient-controlled dosage is provided from the reservoir of the pump.

17. The pump according to claim 16, further comprising a bulkhead, the first flow path being defined in the bulkhead and the patient-controlled pump being disposed in a second flow path from the pump reservoir to the first flow path.

18. The pump according to claim 17, further comprising a safety valve disposed in the second flow path.

19. The pump according to claim 16, wherein the patient-controlled pump is comprised of a deformable crown.

20. The pump according to claim 16, further comprising a regulator for limiting the flow of drug to the patient-controlled pump.

* * * * *